United States Patent
Yamamoto et al.

(10) Patent No.: US 10,324,071 B2
(45) Date of Patent: Jun. 18, 2019

(54) CHROMATOGRAPH MASS SPECTROMETER

(71) Applicant: SHIMADZU CORPORATION, Kyoto-shi, Kyoto (JP)

(72) Inventors: Hideki Yamamoto, Ikeda (JP); Yuko Kobayashi, Kusatsu (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 114 days.

(21) Appl. No.: 15/527,203

(22) PCT Filed: Nov. 17, 2014

(86) PCT No.: PCT/JP2014/080368
§ 371 (c)(1),
(2) Date: May 16, 2017

(87) PCT Pub. No.: WO2016/079790
PCT Pub. Date: May 26, 2016

(65) Prior Publication Data
US 2017/0328874 A1   Nov. 16, 2017

(51) Int. Cl.
*H01J 49/26* (2006.01)
*G01N 30/86* (2006.01)
(Continued)

(52) U.S. Cl.
CPC ......... *G01N 30/8693* (2013.01); *G01N 30/72* (2013.01); *G01N 30/8644* (2013.01);
(Continued)

(58) Field of Classification Search
CPC .............. G01N 30/8693; G01N 30/72; G01N 30/8644; G01N 2030/022; H01J 49/0031; H01J 49/004
(Continued)

(56) References Cited

U.S. PATENT DOCUMENTS 6,900,430 B2   5/2005   Okumura et al.
2003/0066958 A1   4/2003   Okumura et al.
(Continued)

FOREIGN PATENT DOCUMENTS

EP   1 302 973 A3   4/2003
EP   1302973 A2   4/2003
(Continued)

OTHER PUBLICATIONS

Written Opinion for PCT/JP2014/080368 dated Jan. 27, 2015. [PCT/ISA/237].
(Continued)

*Primary Examiner* — Nicole M Ippolito
(74) *Attorney, Agent, or Firm* — Sughrue Mion, PLLC

(57) ABSTRACT

A chromatograph mass spectrometer including: an $MS^{n-1}$ analysis setter for setting an analysis execution period for performing an $MS^{n-1}$ analysis, an execution time for the analysis and a loop time; an analysis period divider for dividing the analysis period into segments according to a change in number or analysis condition of $MS^{n-1}$ analyses to be performed within the same time window; an $MS^n$ analysis setter for performing $MS^{n-1}$ analysis to obtain mass spectrum data and for scheduling $MS^n$ analysis, an ion corresponding to a peak satisfying a set condition being designated as a precursor ion; an $MS^n$ analysis execution time allotter for allotting, in each segment, a time period for execution of the $MS^n$ analysis, the time period being calculated by subtracting an event execution time from the loop time; and an analysis executer for repeatedly performing $MS^{n-1}$ analysis and $MS^n$ analysis in each segment.

7 Claims, 8 Drawing Sheets

(51) Int. Cl.
*G01N 30/72* (2006.01)
*H01J 49/00* (2006.01)
*G01N 30/02* (2006.01)

(52) U.S. Cl.
CPC ........ *H01J 49/004* (2013.01); *H01J 49/0031* (2013.01); *G01N 2030/022* (2013.01)

(58) Field of Classification Search
USPC .................................................. 250/281, 282
See application file for complete search history.

(56) References Cited

U.S. PATENT DOCUMENTS

2012/0191369 A1  7/2012  Yamaguchi
2017/0138916 A1* 5/2017  Sumiyoshi ......... G01N 30/7233

FOREIGN PATENT DOCUMENTS

| EP | 2 418 481 A1 | 2/2012 |
| EP | 1 302 973 B1 | 9/2012 |
| JP | 2003-123685 A | 4/2003 |
| JP | 2003-123686 A | 4/2003 |
| JP | 2006-329881 A | 12/2006 |
| JP | 3990889 B2 | 10/2007 |
| JP | 2010-19665 A | 1/2010 |
| JP | 2011-141220 A | 7/2011 |
| JP | 5293809 B2 | 9/2013 |
| WO | 2008/126383 A1 | 10/2008 |
| WO | 2010/116409 A1 | 10/2010 |

OTHER PUBLICATIONS

Yan et al., "Sensitive and reliable multianalyte quantitation of herbal medicine in rat plasma using dynamic triggered multiple reaction monitoring," Journal of Chromatography B, vol. 928, Mar. 26, 2013, pp. 22-31.
International Search Report of PCT/JP2014/080368, dated Jan. 27, 2015 (PCT/ISA/210).

* cited by examiner

PARENT EVENT EXECUTION PERIOD

ANALYSIS TIME: 0.0-1.0min

ANALYSIS TIME: 1.0-3.0min

ANALYSIS TIME: 3.0-5.0min

ANALYSIS PERIOD SEGMENT I

ANALYSIS PERIOD SEGMENT II

IMPORTANCE ATTACHED TO SPECIFIC EVENT

INTENSITY-BASED

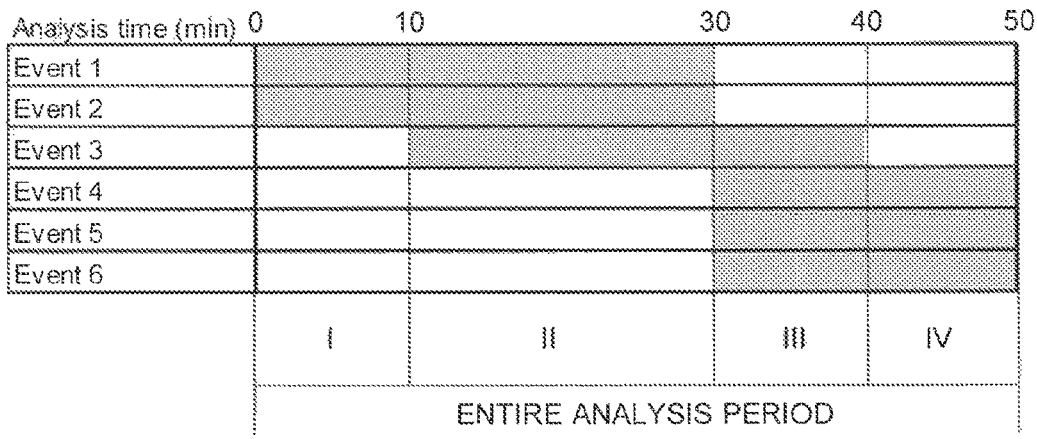

| Analysis period segment | I | II | III | IV |
|---|---|---|---|---|
| Event 1 | 50ms | 33ms | | |
| Event 2 | 50ms | 33ms | | |
| Event 3 | | 33ms | 25ms | |
| Event 4 | | | 25ms | 33ms |
| Event 5 | | | 25ms | 33ms |
| Event 6 | | | 25ms | 33ms |

Fig. 13

| Analysis period segment | I | II | III | IV |
|---|---|---|---|---|
| Event 1 | 500 times | 333 times | | |
| Event 2 | 500 times | 333 times | | |
| Event 3 | | 333 times | 250 times | |
| Event 4 | | | 250 times | 333 times |
| Event 5 | | | 250 times | 333 times |
| Event 6 | | | 250 times | 333 times |

Fig. 14

| Analysis period segment | I | II | III | IV |
|---|---|---|---|---|
| Event 1 | 333 times | 333 times | | |
| Event 2 | 333 times | 333 times | | |
| Event 3 | | 250 times | 250 times | |
| Event 4 | | | 250 times | 250 times |
| Event 5 | | | 250 times | 250 times |
| Event 6 | | | 250 times | 250 times |

CHROMATOGRAPH MASS SPECTROMETER

CROSS REFERENCE TO RELATED APPLICATIONS

This application is a National Stage of International Application No. PCT/JP2014/080368 filed Nov. 17, 2017, the contents of all of which are incorporated herein by reference in their entirety.

TECHNICAL FIELD

The present invention relates to a chromatograph mass spectrometer.

BACKGROUND ART

In a chromatograph mass spectrometer in which a liquid chromatograph or gas chromatograph is combined with a mass spectrometer, i.e. in LC/MS or GC/MS, mass spectra for various components eluted from an LC or GC column with the passage of time can be acquired by repeating a mass spectrometric analysis (MS analysis) over a previously set m/z range.

In the case of a tandem mass spectrometer or an IT-TOF mass spectrometer having an ion trap and time-of-flight mass spectrometer unit, an MS/MS analysis can also be performed in addition to the MS analysis. In these types of mass spectrometers, a technique called the "DDA (data dependent analysis)" or "automatic MS/MS (auto-MS/MS)" is commonly used, in which a precursor ion to be used in the MS/MS analysis is automatically extracted from an MS spectrum obtained by the MS analysis (see Patent Literature 1 or 2).

The DDA is often used to identify unknown compounds in a sample. In this method, a plurality of compounds which may possibly be contained as the unknown compounds are selected as the target compounds with reference to a database which holds the retention time, MS spectrum data and MS/MS spectrum data for a large number of compounds. After that, an analysis schedule is determined as follows:

As one example, the following description assumes that three compounds have been selected as the target compounds: compound A (retention time, 2.5 min), compound B (retention time, 3.5 min) and compound C (retention time, 5.5 min). Initially, for each compound, a mass spectrometric analysis for detecting ions produced from the compound concerned is scheduled for an analysis period having a predetermined width centering on the retention time of the compound (this analysis is hereinafter called the "parent event"). For example, for compound A, an MS analysis (scan analysis) for scanning a mass-to-charge ratio range from m/z=10 to 1000 is scheduled for an analysis period of 0.0-5.0 min. For compound B, an MS analysis for scanning a mass-to-charge ratio range from m/z=1000 to 5000 is scheduled for an analysis period of 1.0-6.0 min. For compound C, an MS analysis for scanning a mass-to-charge ratio range from m/z=5000 to 10000 is scheduled for an analysis period of 3.0-8.0 min. FIG. 1 shows an analysis schedule in which those conditions are set.

Subsequently, the sample is introduced into the chromatograph and the analysis is initiated. After an MS spectrum is obtained by the first measurement performed under the mass spectrometric conditions for compound A, each mass peak which matches the previously set conditions (such a peak is hereinafter described as "satisfying the event conditions") is extracted from one or more mass peaks which have appeared on the MS spectrum. For example, the "previously set conditions" may require that the peak should have an intensity equal to or greater than a previously set threshold and/or its location should correspond to the mass-to-charge ratio of an ion characteristic of compound A. After that, an MS/MS analysis in which an ion corresponding to the extracted mass peak is designated as the precursor ion is performed (this analysis is hereinafter called the "child event") to obtain a mass spectrum of the productions.

An analysis which is performed in the case where three, five and two mass peaks satisfying the event conditions have been respectively found in the parent events related to compounds A, B and C is hereinafter described with reference to FIGS. 2A-2C.

Within the analysis period of 0.0-1.0 min, only the parent event for compound A (this event is labelled as "Pa.A" in the figures) is previously scheduled; three child events 1-3 (which are labelled as "C.A1", etc., in the figures) are added based on the mass spectrum obtained by performing the "Parent A" event. During this analysis period, the "Parent A" event and "Child A1-A3" events are repeated in the mentioned order (FIG. 2A). A measurement in which each of this series of events is executed one time is called the "single measurement", and the period of time required for the single measurement is called the "loop time" (for example, see Patent Literature 3). The measurement data of each event are obtained at intervals of time equal to the loop time.

Within the analysis period of 1.0-3.0 min, the parent events for compounds A and B are previously scheduled, and "Child A1-A3" events and "Child B1-B5" events are added based on the mass spectra obtained by performing those parent events. During this period, the "Parent A" event, "Child A1-A3" events, "Parent B" event, and "Child B1-B5" events are repeated (FIG. 2B). Similarly, during the analysis period of 3.0-5.0 min, the "Parent A" event, "Child A1-A3" events, "Parent B" event, Child B1-B5" events, "Parent C" event, and "Child C1-C2" events are repeated (FIG. 2C).

After the series of measurements has been completed, the mass spectrum data of the product ions obtained in each child event are compared with the MS/MS spectrum data of each target compound registered in the database, and an unknown compound contained in the sample is identified based on the degree of matching of those data. Additionally, a chromatogram is created from the data obtained from each parent event, and the quantity of the identified unknown compound is determined from the chromatogram.

CITATION LIST

Patent Literature

Patent Literature 1: JP 2006-329881 A
Patent Literature 2: JP 2010-19665 A
Patent Literature 3: JP 2011-141220 A
Patent Literature 4: JP 2003-123686 A
Patent Literature 5: WO 2008/126383 A

SUMMARY OF INVENTION

Technical Problem

As explained earlier, the measurement data of each event are obtained at intervals of time equal to the loop time which is the period of time required for the single measurement, and a chromatogram is created from those measurement data.

In the previously described method, since the number of parent and child events to be executed changes depending on the analysis period, each analysis period has a different length of loop time. This causes a variation in the data acquisition interval of a chromatogram created by performing the same event over two or more analysis periods.

Although the previous description is concerned with one example of the case where an MS/MS analysis is automatically performed based on the result of an MS analysis, a similar problem also occurs in any case where an $MS^n$ analysis is automatically performed based on the result of an $MS^{n-1}$ analysis.

In a product ion scan analysis which is performed in the form of an $MS^n$ analysis, the number of data accumulations may be differently set depending on the detection intensity of the precursor ion in the $MS^{n-1}$ analysis. Specifically, when the detection intensity of the precursor ion in the parent event is low, the child event is repeatedly executed and the thereby obtained data are accumulated to improve the detection sensitivity of the product ions (for example, see Patent Literature 4 or 5), or the number of accumulations of a child event in which an ion characteristic of the target compound is designated as the precursor ion is increased to improve the accuracy of the mass spectrum of the product ions. Such a change in the number of data accumulations also causes a variation in the loop time, so that the intervals of the data which constitute the chromatogram vary due to the same reason as described earlier. This problem is not unique to the DDA but may possibly occur in any case where compounds in a sample are analyzed under a plurality of conditions (i.e. when a plurality of events are concurrently executed).

The first problem to be solved by the present invention is to provide a chromatograph mass spectrometer for temporally separating a plurality of components contained in a sample and performing a mass spectrometric analysis of each component, the chromatograph mass spectrometer being capable of performing an $MS^n$ analysis based on the result of an $MS^{n-1}$ analysis of a separated component without causing a variation in the data acquisition interval of the chromatogram due to a change in the number of $MS^{n-1}$ and $MS^n$ analyses depending on the analysis period.

The second problem to be solved by the present invention is to provide a chromatograph mass spectrometer for temporally separating a plurality of components contained in a sample and performing a mass spectrometric analysis of each component, the chromatograph mass spectrometer being free from a variation in the data acquisition interval of the chromatogram due to a change in the number of data accumulations.

Solution to Problem

The first aspect of the present invention developed for solving the first problem is a chromatograph mass spectrometer in which a chromatograph for temporally separating components in a sample is combined with a mass spectrometer capable of performing an $MS^n$ analysis (where n is an integer equal to or greater than two) in which an ion produced by performing, at least one time, a selection and fragmentation of ions produced by ionizing the separated components is subjected to a mass spectrometric analysis, the chromatograph mass spectrometer including:

a) an $MS^{n-1}$ analysis setter for allowing an analysis operator to set an analysis execution period in which an $MS^{n-1}$ analysis for a component separated by the chromatograph is performed within an entire analysis period from the beginning to the end of an analysis, and a loop time which is a data acquisition interval common to all $MS^{n-1}$ analyses;

b) an analysis period divider for dividing the entire analysis period into a plurality of analysis period segments according to the number of $MS^{n-1}$ analyses or contents of analysis conditions of $MS^{n-1}$ analyses to be performed within the same time window;

c) an $MS^n$ analysis setter for performing, in each of the plurality of analysis period segments, an $MS^{n-1}$ analysis to obtain mass spectrum data and extract a mass peak satisfying a previously set condition, and for scheduling an $MS^n$ analysis in which an ion corresponding to the mass peak is designated as a precursor ion;

d) an $MS^n$ analysis execution time allotter for subtracting, in each of the plurality of analysis period segments, an event execution time which is a period of time required for an $MS^{n-1}$ analysis performed within the analysis period segment concerned, from the loop time, and for allotting the remaining time as a period of time in which the $MS^n$ analysis is performed one time; and e) an analysis executer for sequentially and repeatedly performing, in each of the plurality of analysis period segments, an $MS^{n-1}$ analysis and an $MS^n$ analysis scheduled based on the $MS^{n-1}$ analysis.

Specific terms used in the present description in relation to the chromatograph mass spectrometer of the first aspect are hereinafter described.

An "entire analysis period" is the entire period of time from the beginning to the end of an analysis. The analysis execution period of each $MS^{n-1}$ analysis is set as a portion (or the entirety) of this entire analysis period.

An "$MS^{n-1}$ analysis" is an analysis performed for detecting ions produced from a target compound.

An "event execution time" is a period of time for one execution of the $MS^{n-1}$ analysis (e.g. an analysis in which a mass scan is repeated a number of times previously specified for data accumulation). The event execution time may appropriately include a period of time for changing the analysis conditions between two successively performed analyses. For example, the event execution time may be automatically calculated and set based on the $MS^{n-1}$ analysis conditions specified by an analysis operator (e.g. the range of mass-to-charge ratios to be scanned) and the specifications of the device (e.g. scan rate).

An "MS analysis" is an analysis in which an ion corresponding to a mass peak that satisfies a predetermined condition in the mass spectrum data obtained by the $MS^{n-1}$ analysis is designated as the precursor ion.

An "analysis period segment" is set according to a change in the number or analysis condition of $MS^{n-1}$ analyses. For example, if there are two $MS^{n-1}$ analyses "A" and "B" having their respective analysis execution periods overlapping each other, the entire analysis period will be divided into three: an analysis period segment in which $MS^{n-1}$ analysis "A" is solely performed, an analysis period segment in which both of the $MS^{n-1}$ analyses "A" and "B" are performed, and an analysis period segment in which $MS^{n-1}$ analysis "B" is solely performed. By comparison, if the analysis execution period of $MS^{n-1}$ analysis "A" and that of $MS^{n-1}$ analysis "B" are consecutively set, the entire analysis period will be divided into two: an analysis period segment in which $MS^{n-1}$ analysis "A" is solely performed, and an analysis period segment in which $MS^{n-1}$ analysis "B" is solely performed.

Within each analysis period segment, one or more $MS^{n-1}$ analyses (parent events) and one or more $MS^n$ analyses (child events) scheduled in the segment concerned are sequentially and repeatedly performed. In other words, one single measurement in which each of the $MS^{n-1}$ and $MS^n$ analyses is performed one time is carried out. The period of time required for performing this single measurement is the "loop time".

In a chromatograph mass spectrometer of the first aspect, in advance of an analysis, an analysis operator sets an analysis execution period for performing an $MS^{n-1}$ analysis for each of one or more components separated by the chromatograph, as well as a loop time which is a data acquisition interval common to all $MS^{n-1}$ analyses.

Then, the analysis period divider divides the entire analysis period into a plurality of analysis period segments according to a change in the number of $MS^{n-1}$ analyses scheduled in the same time window.

Subsequently, the $MS^n$ analysis setter initiates the analysis, in which each mass peak that satisfies a previously set condition is extracted from the mass spectrum data acquired by performing each $MS^{n-1}$ analysis, and an $MS^n$ analysis in which the ion corresponding to that mass peak is designated as the precursor ion is scheduled. For example, the "previously set condition" may require that the mass peak should have an intensity equal to or higher than a predetermined level and/or that the mass peak should correspond to a mass-to-charge ratio characteristic of the target compound.

After the $MS^n$ analysis has been scheduled, the $MS^n$ analysis execution time allotter subtracts, in each of the plurality of measurement period segments, the event execution time (execution time for the $MS^{n-1}$ analysis) from the loop time and allots the remaining time as the execution time for the $MS^n$ analysis in which the designated precursor ion is used. After the allotment of the execution time to the $MS^n$ analysis is completed, the analysis executer repeatedly performs the $MS^{n-1}$ analysis and $MS^n$ analysis.

In the chromatograph mass spectrometer of the first aspect, the period of time which remains after the event execution time is subtracted from the loop time previously set by an analysis operator is allotted as the execution time for one or more $MS^n$ analyses. Therefore, the loop time remains unchanged even if the number of $MS^{n-1}$ and $MS^n$ analyses changes depending on the analysis period. Accordingly, no variation in the data acquisition interval occurs.

In the chromatograph mass spectrometer of the first aspect, in the case where there are a plurality of $MS^{n-1}$ analyses to be performed within one analysis period segment, with each $MS^{n-1}$ analysis immediately followed by the $MS^n$ analyses which are scheduled based on the result of the $MS^{n-1}$ analysis (e.g. when a "Parent A" event, "Child A1-A3" events, "Parent B" event and "Child B1-B5" events are sequentially executed), it is impossible to allot the execution times to the $MS^n$ analyses ("Child A1-A3" and "Child B1-B5" events) scheduled based on the $MS^{n-1}$ analyses until all $MS^{n-1}$ analyses (both "Parent A" and "Parent B" events) are completed.

Accordingly, the chromatograph mass spectrometer of the first aspect may preferably be configured so that:

in the case where a plurality of $MS^{n-1}$ analyses are scheduled in the analysis period segment, the $MS^n$ analysis execution time allotter divides the loop time into loop-time segments which respectively correspond to the plurality of $MS^{n-1}$ analyses, subtracts the event execution time of the corresponding $MS^{n-1}$ analysis from each loop-time segment, and allots the remaining time as the execution time for each of $MS^n$ analyses scheduled based on the result of the $MS^{n-1}$ analysis.

By this configuration, in the case where a plurality of $MS^{n-1}$ analyses are scheduled in one analysis period segment and sequentially performed in the aforementioned order, the execution time for the $MS^n$ analyses which are scheduled based on the result of an $MS^{n-1}$ analysis can be allotted immediately after the $MS^{n-1}$ analysis is completed.

In a chromatograph mass spectrometer, an identification of an unknown compound by the $MS^{n-1}$ and $MS^n$ analyses may be concurrently performed with a quantitative determination of a known compound by an SIM (selected ion monitoring) or MRM (multiple reaction monitoring) analysis.

Accordingly, in a preferable mode of the chromatograph mass spectrometer of the first aspect:

the analysis period divider divides the entire analysis period into a plurality of analysis period segments according to a change in the number of $MS^{n-1}$ analyses scheduled in the same time window and a change in the number of specific-ion analyses for selectively detecting an ion having a specific mass-to-charge ratio; and the $MS^n$ analysis execution time allotter subtracts, in each of the plurality of analysis period segments, the event execution time plus an execution time for the specific-ion analyses from the loop time, and allots the remaining time as the execution time for each of the scheduled $MS^n$ analyses.

By this configuration, even in the case where the identification of an unknown compound contained in a sample and a quantitative determination of a known compound are concurrently performed, the loop time will be constantly maintained, so that the data will be acquired at regular intervals of time.

The second aspect of the present invention developed for solving the second problem is a chromatograph mass spectrometer in which a chromatograph for temporally separating components in a sample is combined with a mass spectrometer for performing a mass spectrometric analysis of ions produced from the separated components, the chromatograph mass spectrometer including:

a) a mass spectrometry setter for allowing an analysis operator to set an analysis execution period in which each of a plurality of mass spectrometric analyses for the components separated by the chromatograph is performed within an entire analysis period from the beginning to the end of an analysis, and a loop time which is a data acquisition interval common to all mass spectrometric analyses;

b) an analysis period divider for dividing the entire analysis period into a plurality of analysis period segments according to a change in the number or analysis condition of mass spectrometric analyses performed within the same time window;

c) an allotted execution time setter for setting, in each of the plurality of analysis period segments, an allotted execution time of each mass spectrometric analysis by dividing the loop time into the number of mass spectrometric analyses scheduled in the analysis period segment concerned;

d) an analysis repetition number setter for setting, in each of the plurality of analysis period segments, the number of repetitions of each mass spectrometric analysis based on the allotted execution time and a basic execution time required for one execution of the mass spectrometric analysis scheduled in the analysis period segment concerned; and e) an analysis executer for repeatedly executing, in each of the plurality of analysis period segments, an analysis in which each mass spectrometric analysis is performed up to the aforementioned number of repetitions.

Specific terms used in the present description in relation to the chromatograph mass spectrometer of the second aspect are hereinafter described.

A "basic execution time" is a period of time necessary for one execution of the mass spectrometric analysis, which is normally equal to the minimum period of time to perform the analysis (e.g. the period of time required for an analysis in which a mass scan is performed one time). The basic execution time may appropriately include a period of time for changing the analysis conditions between two successively executed events. For example, the basic execution time may be automatically calculated and set based on the mass spectrometric analysis conditions specified by an analysis operator (e.g. the range of mass-to-change ratios to be scanned) and the specifications of the device (e.g. scan rate).

"Analysis period segments" are segments of time obtained by dividing the entire analysis period into a plurality of segments according to a change in the number or analysis condition of the mass spectrometric analyses (events) to be performed. In each analysis period segment, a series of events scheduled in the analysis period segment concerned is repeatedly executed.

It should be noted that the chromatograph mass spectrometer of the second aspect repeatedly performs a measurement which includes a series of events, with each event continuously repeated the number of times set by the analysis repetition number setter. For example, one set of measurements which includes event 1 continuously executed 100 times followed by event 2 continuously executed 200 times is repeatedly performed. This one set of measurements is the single measurement. The period of time required for performing the single measurement is the "loop time".

In the chromatograph mass spectrometer of the second aspect, an analysis operator initially sets the analysis execution period in which mass spectrometric analyses for analyzing components in a sample are performed, as well as the loop time common to all mass spectrometric analyses. The basic execution time may be automatically obtained by the device based on the contents of the mass spectrometric analysis conditions (e.g. the range of mass-to-charge ratios to be scanned) and the specifications of the device (e.g. scan rate). Then, the entire analysis period is divided into a plurality of analysis period segments according to a change in the number of mass spectrometric analyses scheduled in the same time window.

Subsequently, the allotted execution time setter sets the allotted execution time for each mass spectrometric analysis according to the loop time and the number of mass spectrometric analyses scheduled in each analysis period segment. Then, the analysis repetition number setter sets the number of repetitive executions of each mass spectrometric analysis within each analysis period segment based on the allotted execution time and the basic execution time. For example, the number of repetitive executions may be the number obtained by dividing the allotted execution time by the basic execution time.

After the number of repetitive executions of each mass spectrometric analysis within each analysis period segment has been set, the analysis executer initiates the analysis. In each analysis period segment, an analysis in which each mass spectrometric analysis is performed up to the aforementioned number of repetition times is repeatedly performed. It should be noted that, in the chromatograph mass spectrometer of the present aspect, an analysis in which one mass spectrometric analysis is performed up to the aforementioned number of repetition times is handled as one event.

In the chromatograph mass spectrometer of the second aspect, the allotted execution time of each mass spectrometric analysis is set by dividing the loop time previously set by the analysis operator into the number of mass spectrometric analyses scheduled in each analysis period segment. Each mass spectrometric analysis is repeatedly performed within the allotted execution time. Therefore, even in the case where the number of data accumulations is changed, the loop time will be constantly maintained, so that the data will be acquired at regular intervals of time.

In the chromatograph mass spectrometer of the second aspect, the analysis repetition number setter may also be configured so as to set the number of repetitions of each mass spectrometric analysis so that a mass spectrometric analysis performed over a plurality of analysis period segments under the same condition is always performed with a fixed number of repetitions of the analysis.

As one example of this mode of the present invention, consider the following case: with the loop time set at 100 msec, a mass spectrometric analysis with a basic execution time of 100 µsec is scheduled to be performed over a period of time which spans two analysis period segments, with two and three mass spectrometric analyses scheduled to be performed in these two analysis period segments "A" and "B", respectively. In this case, the largest possible number of repetitions of the analysis in each analysis period segment is 500 and 333, respectively. In this case, the number of repetitions can be uniformly set at 333 in both analysis period segments "A" and "B" by allotting 150 µsec for each execution of the mass spectrometric analysis within the analysis period segment "A" and 100 µsec for each execution of mass spectrometric analysis within the analysis period segment "B".

Alternatively, within the analysis period segment "A", a standby period of 50 µsec may be provided after each completion of the mass spectrometric analysis performed for the basic execution time of 100 µsec. It is also possible to provide a standby period of 17 msec within the analysis period segment "A" and thereby make the execution time of the mass spectrometric analysis uniformly set at 33 msec in both analysis period segments "A" and "B" so that the number of repetitions will be uniformly set at 333 in both analysis period segments. For example, such standby periods can be appropriately set by the analysis repetition number setter in conjunction with a software application on a computer as well as the present device.

It should be noted that the chromatograph mass spectrometers of the first and second aspects are both based on the common technical idea of constantly maintaining the loop time and acquiring data at regular intervals of time even in the case where the number of mass spectrometric analyses to be performed changes depending on the analysis period.

Advantageous Effects of the Invention

With the chromatograph mass spectrometer according to the first aspect of the present invention, it is possible to constantly maintain the loop time and acquire data at regular intervals of time even in the case where the number of $MS^{n-1}$ and $MS^n$ analyses changes depending on the analysis period.

With the chromatograph mass spectrometer according to the second aspect of the present invention, it is possible to constantly maintain the loop time and acquire data at regular intervals of time even in the case where the number of data accumulations is changed.

BRIEF DESCRIPTION OF DRAWINGS

FIG. 11 is a diagram showing an analysis schedule in the third embodiment.

FIG. 12 is one example of the allotted execution time in the third embodiment.

FIG. 13 is one example of the setting of the number of repetitions of the analysis in the third embodiment.

FIG. 14 is another example of the setting of the number of repetitions of the analysis in the third embodiment.

DESCRIPTION OF EMBODIMENTS

Specific embodiments of the chromatograph mass spectrometer according to the present invention are hereinafter described with reference to the attached drawings.

First Embodiment

Figure 1:
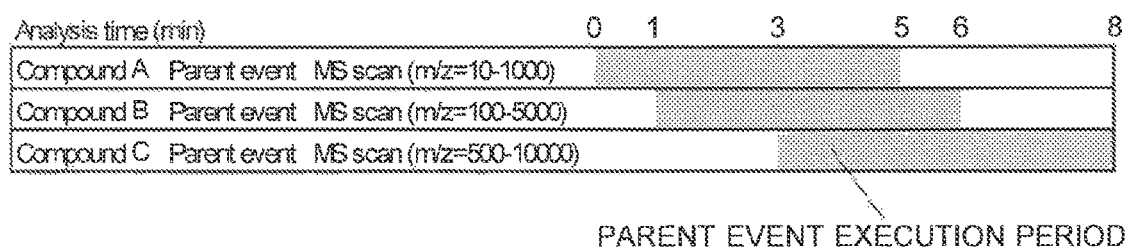
FIG. 1 is one example of the analysis schedule in a chromatograph mass spectrometer.
Figure 2A:
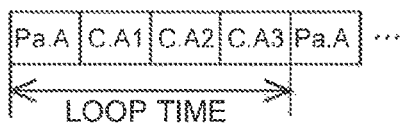
FIGS. 2A-2C are diagrams illustrating the loop time in a conventional chromatograph mass spectrometer.
Figure 2B:
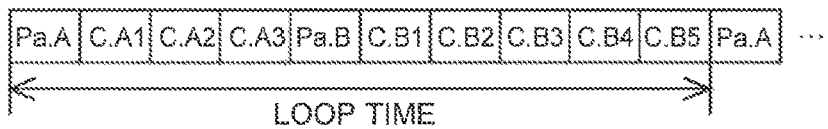
Figure 2C:
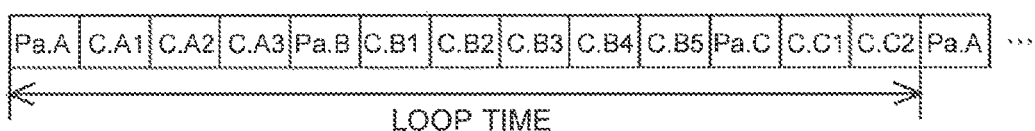
Figure 3:
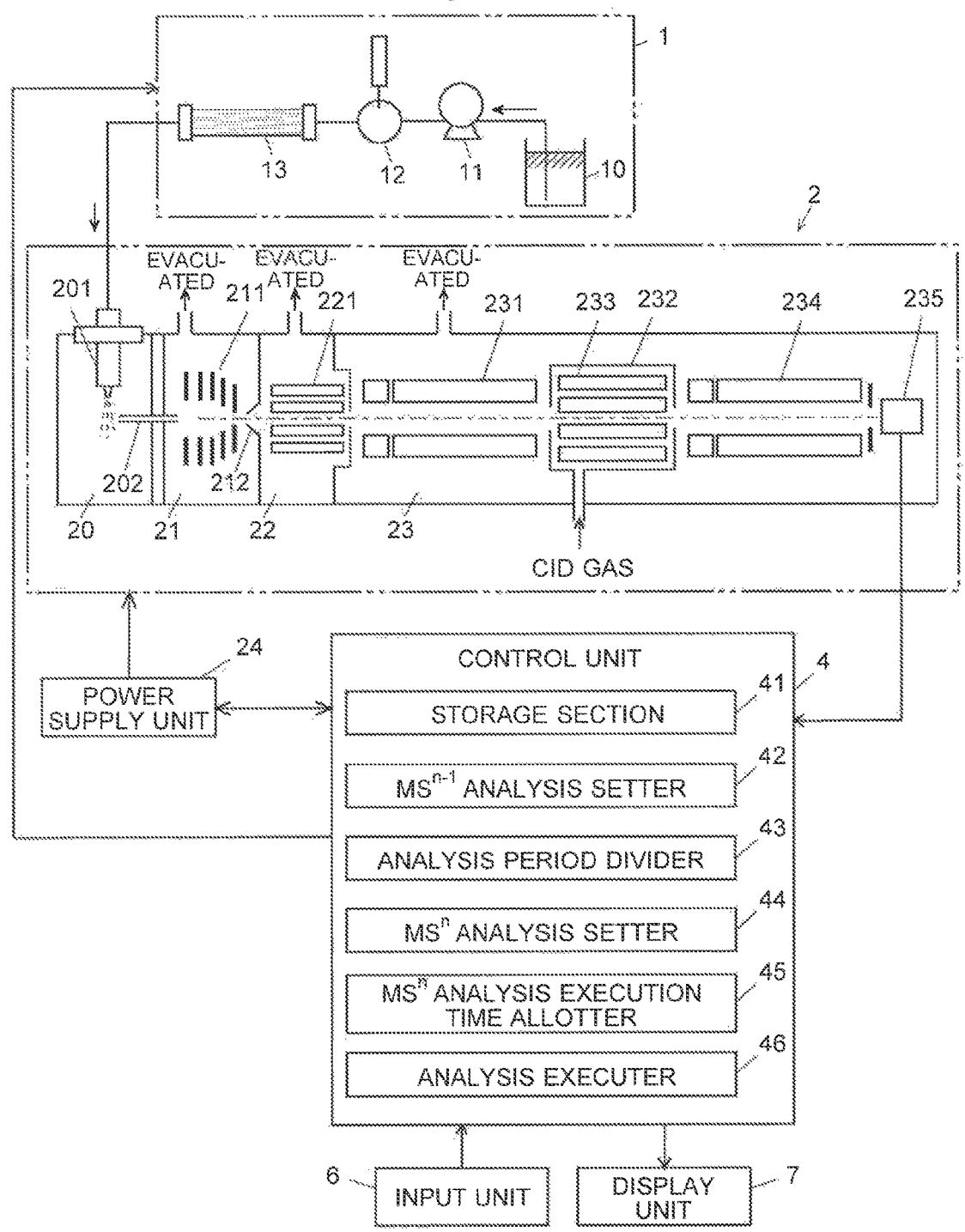
FIG. 3 is a configuration diagram of the main components of a liquid chromatograph mass spectrometer of the first embodiment.

The chromatograph mass spectrometer of the first embodiment is a liquid chromatograph mass spectrometer composed of a liquid chromatograph unit 1, mass spectrometer unit 2, and control unit 4 for controlling the operations of these units. FIG. 3 is a configuration diagram of its main components.

In the liquid chromatograph mass spectrometer of the first embodiment, the liquid chromatograph unit 1 includes a mobile phase container 10 in which a mobile phase is stored, a pump 11 for drawing the mobile phase and supplying it at a fixed flow rate, an injector 12 for injecting a predetermined amount of prepared sample liquid into the mobile phase, and a column 13 for temporally separating various compounds contained in the sample liquid.

The mass spectrometer unit 2 has the configuration of a multi-stage differential pumping system including an ionization chamber 20 maintained at approximately atmospheric pressure and an analysis chamber 23 evacuated to a high degree of vacuum by a vacuum pump (not shown), between which first and second intermediate vacuum chambers 21 and 22 are provided having their degrees of vacuum increased in a stepwise manner. The ionization chamber 20 is provided with an electrospray ionization probe (ESI probe) 201 for spraying a sample solution while imparting electric charges to the same solution. The ionization chamber 20 communicates with the first intermediate vacuum chamber 21 in the next stage via a thin heated capillary 202. The first intermediate vacuum chamber 21 is separated from the second intermediate vacuum chamber a skimmer 212 having a small hole at its apex. The first and second intermediate vacuum chambers 21 and 22 respectively contain ion guides 211 and 221 for transporting ions to the next stage while converging the ions. The analysis chamber 23 contains a front quadrupole mass filter (Q1) 231 which separates ions according to their mass-to-charge ratios and a rear quadrupole mass filter (Q3) 234 which also separates ions according to their mass-to-charge ratios, with a collision cell 232 containing a multipole ion guide (q2) 233 placed between the two mass filters, as well as an ion detector 235.

A CID gas, such as argon or nitrogen, can be continuously or intermittently supplied into the collision cell 232. A power supply unit 24 applies predetermined voltages to the ESI probe 201, ion guides 211, 221 and 233, quadrupole mass filters 231 and 234 as well as other elements, respectively. In each of the quadrupole mass filters 231 and 234, pre-rod electrodes for correcting the disturbance of the electric field at the inlet end are provided before the main rod electrodes. A voltage which is different from those applied to the main rod electrodes can be applied to the pre-rod electrodes.

The mass spectrometer unit 2 can perform various measurements, such as an MS scan measurement, SIM measurement, MS/MS scan measurement and MRM measurement. In the MS scan measurement and SIM measurement, the front quadrupole mass filter (Q1) 231 is prevented from functioning as a mass filter (i.e. it allows all ions to pass through); the rear quadrupole mass filter (Q3) 234 is made to solely function as a mass filter. In the MS scan measurement, the mass-to-charge ratio of the ion to be allowed to pass through the rear quadrupole mass filter 234 is continuously changed. In the SIM measurement, the mass-to-charge ratio of the ion to be allowed to pass through the rear quadrupole mass filter 234 is fixed.

On the other hand, in the MS/MS scan measurement (product ion scan measurement) and MRM measurement, the front quadrupole mass filter (Q1) 231 and rear quadrupole mass filter (Q3) 234 are both made to function as the mass fitters. The front quadrupole mass filter (Q1) 231 allows only an ion designated as the precursor ion to pass through. Additionally, the CID gas is supplied into the collision cell 232 so as to fragment the precursor ion into product ions. In the MS/MS scan measurement, the mass-to-charge ratio of the ion to be allowed to pass through the rear quadrupole mass filter (Q3) 234 is continuously changed. In the MRM measurement, the mass-to-charge ratio of the ion to be allowed to pass through the rear quadrupole mass filter (Q3) 234 is fixed.

The control unit 4 has a storage section 41 and the following functional blocks: an $MS^{n-1}$ analysis setter 42, analysis period divider 43, $MS^n$ analysis setter 44, $MS^n$ analysis execution time allotter 45 and analysis executer 46. The same unit also has the function of controlling the operations of the relevant elements, such as the pump 11 and injector 12 in the liquid chromatograph unit 1 as well as the power supply unit 24 and CID gas supplier (not shown) in the mass spectrometer unit 2, in accordance with the operations of those functional blocks. The control unit 4 is actually a personal computer, which can fulfil the functions as the control unit 4 by executing a data-processing software program previously installed on this computer. The control unit 4 has an input unit 6 and display unit 7 connected to it.

Figure 4:
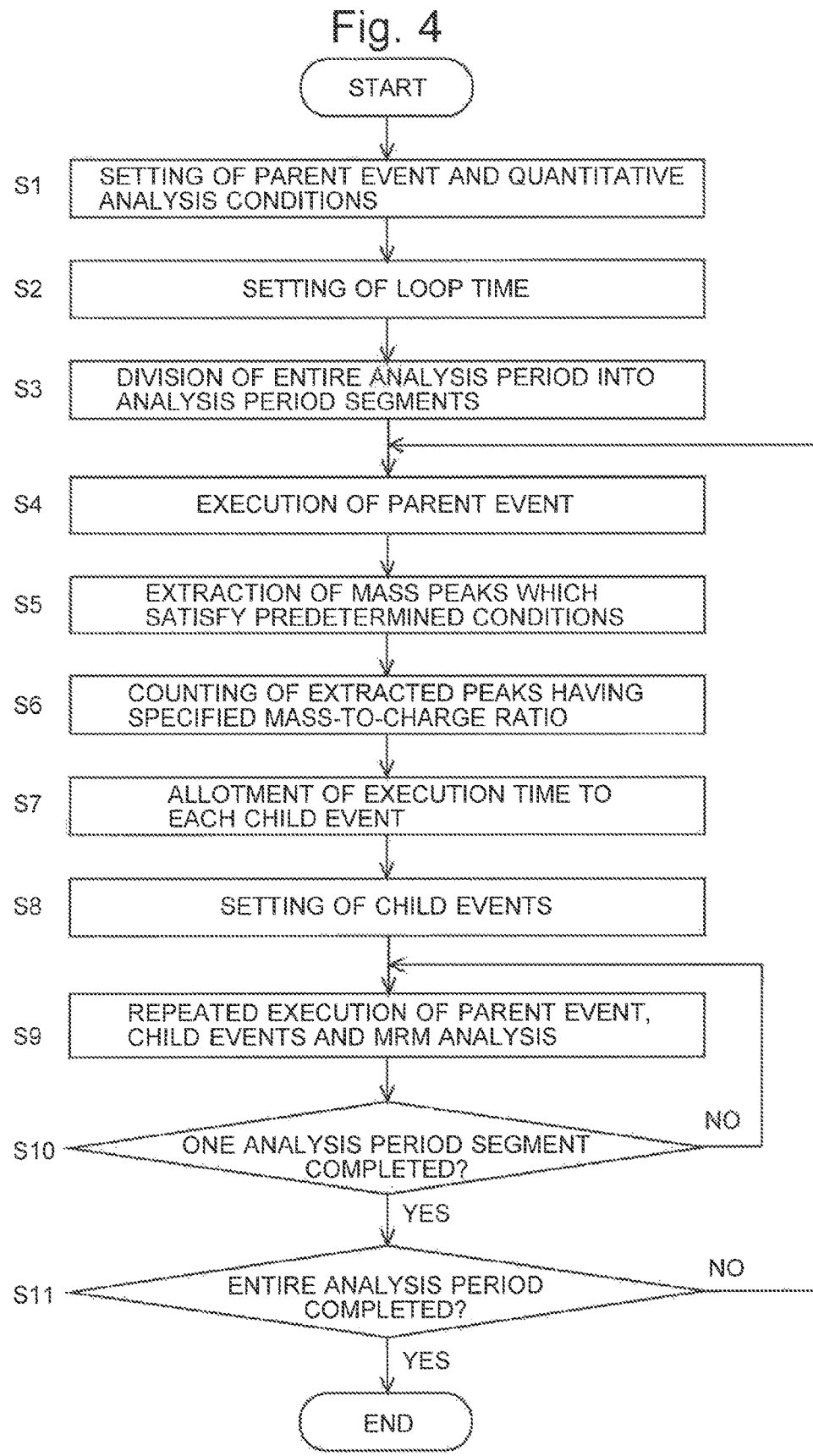
FIG. 4 is a flowchart illustrating the analytical procedure in the liquid chromatograph mass spectrometer of the first embodiment.

A procedure of an analysis using the liquid chromatograph mass spectrometer of the present embodiment is hereinafter described with reference to the flowchart of FIG. 4. In the present embodiment, both the identification of unknown compounds contained in a sample and the quantitative determination of a known compound (compound D) contained in the sample are concurrently performed. DDA is used to identify the unknown compound, while MRM is used to determine the quantity of compound D.

The compounds which are supposed to exist as unknown compounds ("target compounds") are compounds A-C. The identification analysis conditions for the target compounds (such as the analysis execution time, event execution time (period of time required for the analysis) and MS scan range) and the quantitative analysis conditions for the known compound (such as the analysis execution time, event execution time and MRM conditions) are previously specified and stored in the storage section 41. Specifically, the identification analysis conditions stored for the target compounds are as follows: For compound A, a positive ion scan analysis for detecting positive ions with mass-to-charge ratios of 10-1000 is scheduled for the period of 0.0-1.0 min; for compound B, a positive ion scan analysis for detecting positive ions with mass-to-charge ratios of 100-5000 is scheduled for the period of 1.0-5.0 min; and for compound C, a positive ion scan analysis for detecting positive ions with mass-to-charge ratios of 5000-10000 is scheduled for the period of 5.0-8.0 min, as well as a negative ion scan analysis for detecting negative ions with mass-to-charge ratios of 5000-10000 for the same period of time. In any of these scan analyses, the event execution time is 300 msec. The quantitative analysis conditions stored for compound D is an MRM analysis (event execution time, 300 msec) in which a precursor ion having a mass-to-charge ratio of D1 is selectively allowed to pass through the front quadrupole mass filter (Q1) 231 while a product ion having a mass-to-charge ratio of D2 is selectively allowed to pass throb the rear quadrupole mass filter (Q3) 234.

Initially, the $MS^{n-1}$ analysis setter 42 displays, on the display unit 7, a window for prompting an analysis operator to set analysis conditions and loop time. On this display, the analysis operator sets analysis conditions for compounds A-D read from the storage section 41 (Step S1). Specifically, the analysis operator sets MS scan analyses for compounds A-C which are the target compounds assumed as unknown compounds (these analyses are hereinafter called the "parent events") and an MRM analysis for compound D which is the known compound. After the parent events have been set by the analysis operator, the $MS^{n-1}$ analysis setter 42 automatically reads the event execution times of the parent events from the storage section 41 and sets those event execution times.

Figure 5:
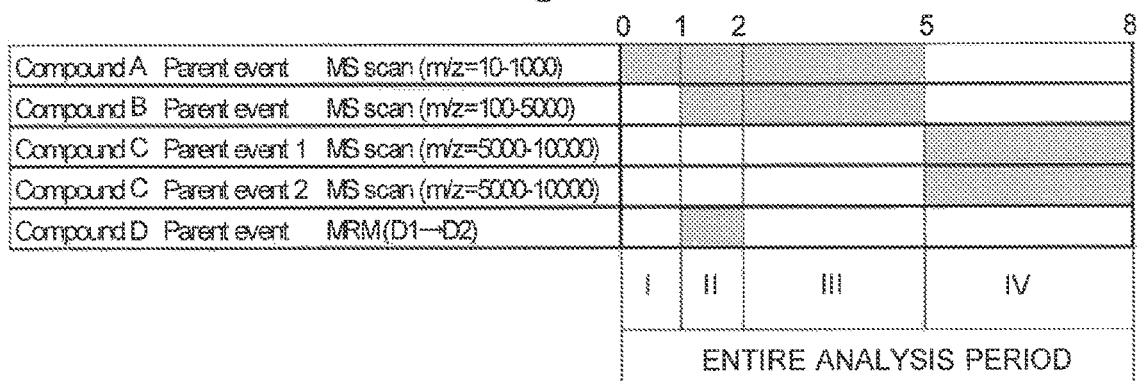
FIG. 5 is a diagram showing an analysis schedule in the first embodiment.

The analysis operator also sets the loop time (in the present embodiment, 3.0 sec) which determines the data intervals at which the analysis data should be acquired (Step S2). After these setting tasks are completed, the analysis period divider 43 divides the entire analysis period into analysis period segments according to a change in the number of $MS^{n-1}$ analyses scheduled in each time window. As a result, an analysis schedule as shown in FIG. 5 is created. The entire analysis period is divided as follows: analysis period segment I (0.0-1.0 min; number of analyses, 1), analysis period segment II (1.0-2.0 min; number of analyses, 3), analysis period segment III (2.0-5.0 min; number of analyses, 2) and analysis period segment IV (5.0-8.0 min; number of analyses, 2). As in the analysis period segments III and IV, analysis period segments in which the same number of analyses are performed should yet be treated as separate analysis period segments if the contents of those analyses are different (Step S3).

When the analysis operator commands the initiation of the analysis, the $MS^n$ analysis setter 44 executes the scheduled parent events. Within the analysis period segment I, the MS scan analysis for compound A ("Parent A" event) is performed (Step S4), where the MS spectrum data are acquired and sequentially stored in the storage section 41. In parallel with the acquisition of the MS spectrum data, each mass peak which satisfies predetermined conditions (e.g. whose intensity is equal to or higher than a predetermined level, or which corresponds to an ion characteristic of compound A) is extracted from the data (Step S5). For each extracted mass peak, the mass-to-charge ratio of the corresponding ion is determined and stored in the storage section 41. After the completion of the MS scan analysis ("Parent A" event), the mass-to-charge ratios stored in the storage section 41 are read and counted (Step S6).

After the completion of the counting, the $MS^n$ analysis execution time allotter 45 subtracts the time required for the parent event from the loop time which was set before the analysis, divides the remaining time by the counted number of extracted mass peaks (the number of mass-to-charge ratios stored in the storage section 41), and allots the obtained time as the execution time to each MS/MS analysis (product ion scan analysis, which is hereinafter called the "child event") in which an ion corresponding to one of those mass-to-charge ratios is designated as the precursor ion (Step S7). The range of mass-to-charge ratios to be scanned in the product ion scan analysis is, for example, automatically set at the range from zero to the mass-to-charge ratio of the precursor ion. In the analysis period segment I of the present embodiment, three mass peaks are extracted for compound A. Accordingly, a period of 900 msec, which is obtained by subtracting the time required for the parent event (300 msec) from the loop time (3 sec) and dividing the remaining time (2700 msec) by three, is allotted to each of the "Child A1-A3 (C.A1-A3)" events, i.e. the MS/MS analyses which respectively correspond to the three mass peaks (see FIG. 6A).

If there are many child events, the period of time allotted to each child event may become too short to acquire a sufficient amount of data in the product ion scan analysis. Accordingly, if a large number of child events are expected to be spawned from the parent event, the analysis operator additionally sets the minimum length of time to be allotted per child event (minimum child-event execution time) along with the loop time in Step S2.

Provided that the minimum child-event execution time is set by the analysis operator, if the execution time allotted to the child events in Step S7 has become shorter than the minimum child-event execution time, the $MS^n$ analysis execution time allotter 45 cancels (deletes) the child event in which the ion having the lowest intensity in the mass spectrum obtained in the parent event is designated as the precursor ion, and recalculates the execution time to be allotted to the child events. At this point in time, if the execution time of the child events is still shorter than the minimum child-event execution time, the child event in which an ion having the second lowest intensity in the parent spectrum is designated as the precursor ion is cancelled, and the execution time is recalculated. As a result of repeating such a process, when the execution time of the child events has become longer than the minimum child-event execution time, the $MS^n$ analysis execution time allotter 45 fixes the analysis execution times of all events.

In the previous description, the deletion is performed in ascending order of the intensity in the mass spectrum obtained in the parent event. When the analysis operator can previously predict the mass-to-charge ratios of the ions which will appear on the mass spectrum obtained in the parent event, it is preferable to previously set the priorities of the mass-to-charge ratios of those ions and configure the system to sequentially delete child events in ascending order of the priority of the mass-to-charge ratio of the ion designated as the precursor ion.

After the analysis execution times of all events have been fixed, the analysis executer 46 repeatedly performs the parent and child events (Step S9). At every completion of one repetition, if the current analysis period segment has been completed ("YES" in Step S10), the analysis executer subsequently determines whether or not all analysis period segments have been completed (Step S11). If not all analysis period segments have been completed ("NO" in Step S11), the operation proceeds to the next analysis period segment and the sequential process from Step S4 is performed once more.

For the other analysis period segments, all events are similarly set by the previously described procedure, i.e. by executing the parent event, extracting the mass peaks which satisfy the predetermined conditions, determining the mass-to-charge ratios corresponding to those mass peaks, counting the extracted peaks, allotting the execution time to the child events, and setting the child events. Then, those events are repeatedly executed.

However, as in the analysis period segment II, if a plurality of parent events are scheduled, and if a quantitative analysis (e.g. MRM measurement) is included in them, the process becomes different. In this case, the execution time required for the MRM analysis (300 msec) is initially subtracted from the loop time (3 sec), and the remaining time (2700 msec) is divided by the number of parent events (2) to obtain a time value (1350 msec). Subsequently, the execution time of the "Parent A (Pa.A)" event (300 msec) is subtracted from 1350 msec, and the remaining time is equally allotted as the execution times to the "Child A1-A3 (C.A1-A3)" events, i.e. 350 msec to each child event. Similarly, the execution time of the "Parent B (Pa.B)" event (300 msec) is subtracted from 1350 msec, and the remaining time is equally allotted as the execution times to the "Child B1-B5 (C.B1-B5)" events, i.e. 210 msec for each child event (see FIG. 6B). After the execution times of all events have been fixed, the analysis executer 46 repeatedly performs the parent and child events until the analysis period segment concerned is completed.

Figure 6A:
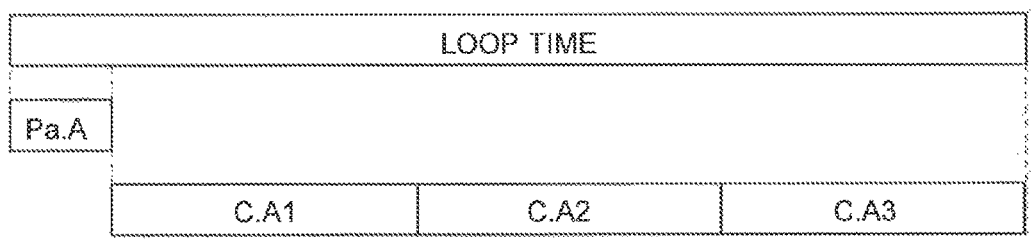
FIGS. 6A and 6B are diagrams illustrating an allotment of the analysis execution time in the first embodiment.
Figure 6B:
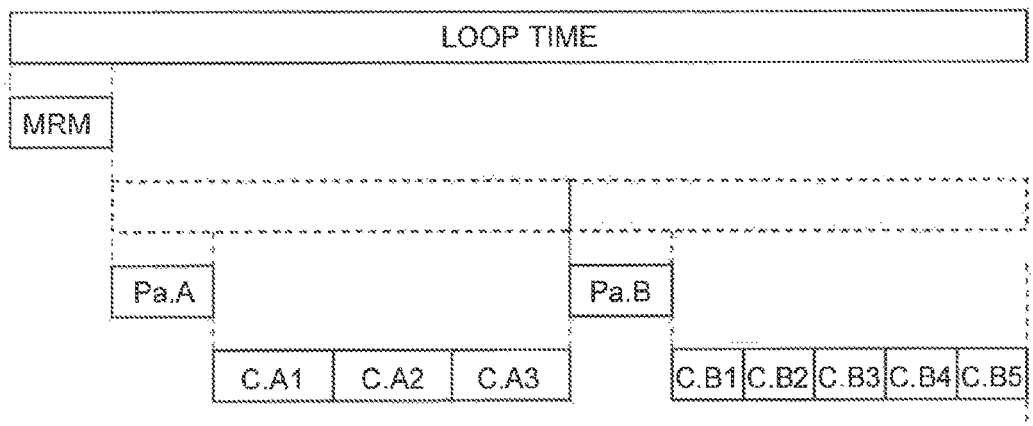

In the chromatograph mass spectrometer of the present embodiment, as can be seen in FIGS. 6A and 6B, the loop time is constantly maintained regardless of the number of parent events scheduled in the same time window, the number of child events spawned from those parent events, and presence or absence of an MRM analysis. Therefore, the data for constructing a chromatogram will be obtained at regular intervals of time.

Second Embodiment

Subsequently, a liquid chromatograph mass spectrometer of the second embodiment is described. The liquid chromatograph mass spectrometer of the second embodiment differs from that of the first embodiment in the method by which the MS$^n$ analysis execution time allotter 45 allots the execution times to the child events. It should be noted that the descriptions concerning the configurations and operations which are common to the first and second embodiments will be appropriately omitted from the descriptions of the second embodiment.

In the liquid chromatograph mass spectrometer of the second embodiment, the analysis operator selects an execution-time allotment method in addition to the loop time in the previously described Step S2. Three methods for allotting the execution time are prepared beforehand: "equal division", "importance attached to specific event" and "intensity-based allotment". The analysis operator selects one of these methods. The selection may be applied as the common allotment method for all parent events, or one allotment method may be independently selected for each parent event.

In the second embodiment, m/z=235.25 is specified by the analysis operator as the mass-to-charge ratio of the ion characteristic of the target compound A. Furthermore, as a condition to generate "Child A (C.A)" events, it is required that the peak intensity on the mass spectrum data obtained by executing the "Parent A (Pa.A)" event should be equal to or higher than 10,000.

If the analysis operator selects the "equal division", the same operation as in the first embodiment is performed: i.e. the MS$^n$ analysis execution time allotter 45 subtracts the time required for the parent event from the loop time and equally allots the remaining time as the execution times to the child events. The description in the second embodiment is concerned with the case where the analysis operator has selected the "importance attached to specific event" or "intensity-based allotment".

Figure 7:
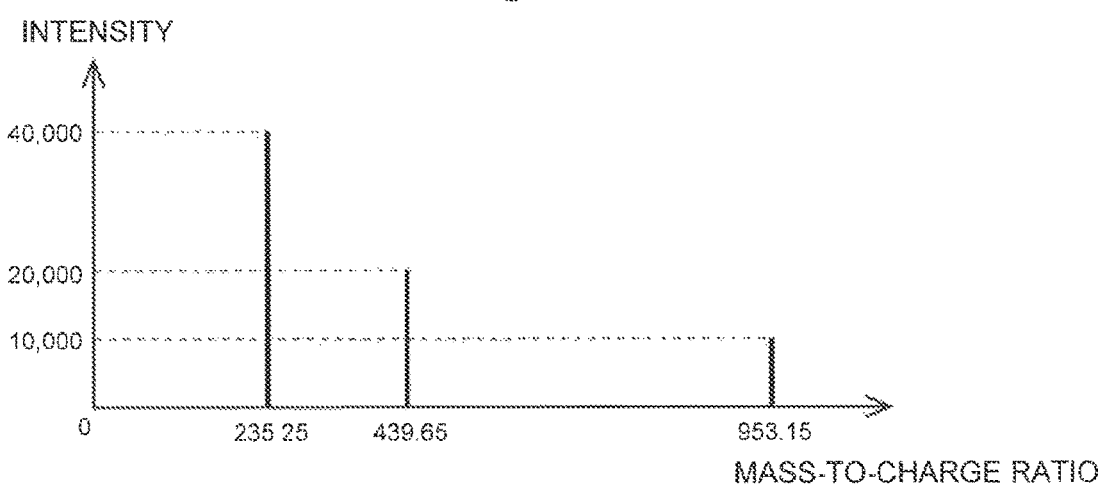
FIG. 7 is a mass spectrum obtained by executing a "Parent A" event in the second embodiment.

Hereinafter, the case where the mass spectrum data as shown in FIG. 7 have been obtained by the "Parent A" event for compound A executed by the MS$^n$ analysis setter 44 is described as one example. In the mass spectrum data shown in FIG. 7, a mass peak which corresponds to the mass-to-charge ratio previously specified by the analysis operator (m/z=235.25) is present. Including this peak, a total of three mass peaks have intensities equal to or higher than 10,000.

Figure 8A:
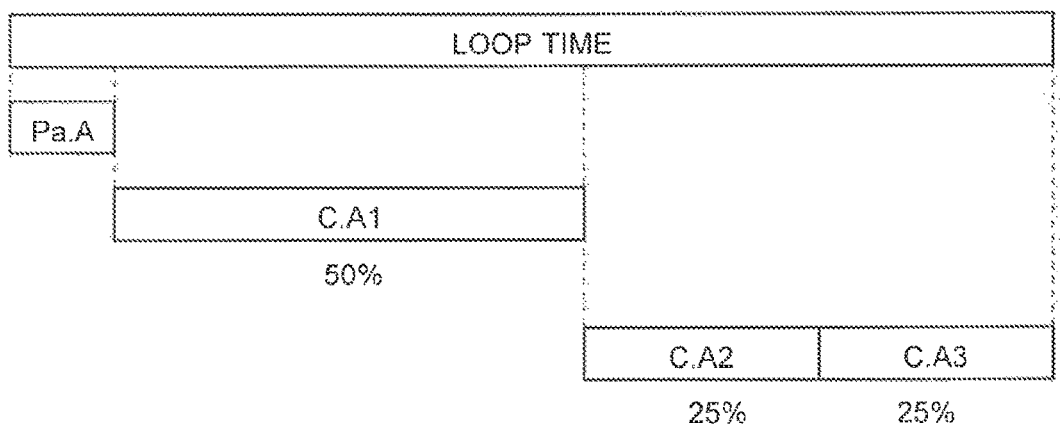
FIGS. 8A and 8B are diagrams illustrating an allotment of the analysis execution time in the second embodiment.

If the analysis operator selects the "importance attached to specific event" as the execution-time allotment method, the MS$^n$ analysis execution time allotter 45 allots the execution times to the child events as follows: Initially, the event time of the parent event (300 msec) is subtracted from the loop time (3 sec) to obtain the remaining time (2700 msec). Subsequently, 50% (1350 msec) of the remaining time is allotted to the "specific event", i.e. the child event in which the previously designated ion characteristic of the target compound A is designated as the precursor ion. The rest of the time is equally allotted (675 msec per event) to the two child events in which the ions corresponding to the two other mass peaks are respectively designated as the precursor ions (see FIG. 8A).

This execution-time allotment method called the "importance attached to specific event" is a method in which an especially long period of time is allotted to a "specific" event, i.e. a child event in which an ion designated as an important ion by the analysis operator before the analysis (e.g. an ion characteristic of the target compound) is designated as the precursor ion. When this method is selected, the product ion scan measurement designated as the specific event is performed at a lower scan rate so that product ions can be obtained at a higher mass accuracy. In the previous description, there is only one specific event, to which 50% of the time which remains after the time required for the parent event is subtracted from the loop time is allotted. However, there may be two or more specific events, and the percentage to be allotted to those specific events can be appropriately set by the analysis operator before the analysis. For example, the setting may be such that 40% is allotted to one specific event in which an ion having a mass-to-charge ratio of α is designated as the precursor ion, while 30% designated as the precursor ion, with the remaining 30% allotted to the other child events.

Figure 8B:
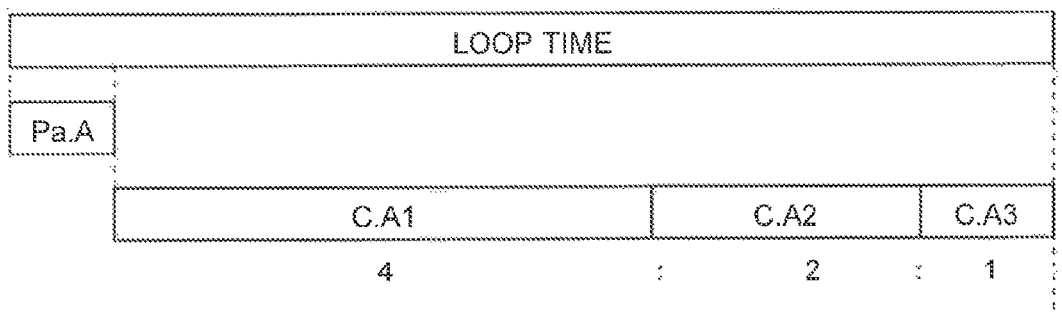

If the analysis operator selects the "intensity-based allotment" as the execution-time allotment method, the MS$^n$ analysis execution time allotter 45 allots the execution times to the child events as follows: Initially, the event time of the parent event is subtracted from the loop time (3 sec) to obtain the remaining time (2700 msec). This remaining time is subsequently divided at the intensity ratio of the three mass peaks and allotted as the execution times to the child events in which the ions corresponding to those mass peaks are respectively designated as the precursor ions. More specifically, the execution time is allotted at the ratio of 4:2:1, or 1543 msec, 77 msec and 386 msec, to the "Child A1 (C.A1)" event (corresponding to the mass peak with an intensity of 40,000) in which an ion having a mass-to-charge ratio of m/z=235.25 is designated as the precursor ion, "Child A2 (C.A2)" event (corresponding to the mass peak with an intensity of 20,000) in which an ion having a mass-to-charge ratio of m/z=439.65 is designated as the precursor ion, and "Child A3 (CA:3)" event (corresponding to the mass peak with an intensity of 10,000) in which an ion having a mass-to-charge ratio of m/z=953.15 is designated as the precursor ion (see FIG. 8B).

This execution-time allotment method called the "intensity-based allotment" is a method in which the execution time is allotted to each child event according to the amount of generated precursor ion. When this method is selected, a child event in which a large amount of precursor ion is generated so that a large amount of product ions derived from the precursor ion are likely to be detected is executed at a lower scan rate, so that the product ions can be obtained at a high mass accuracy. As opposed to the previous description in which the intensity ratio of the mass peaks is directly used for the allotment of the execution time to the child events, a logarithmic ratio of the intensities of the mass peaks may be used for the allotment of the execution times to the child events: For example, when there are three mass peaks with an intensity ratio of 100,000, 10,000 and 1,000, the execution time is allotted at a ratio of 3:2:1 to the three corresponding child events. The analysis operator can configure the system so that the execution time is allotted using the intensities of the mass peaks in other appropriate manners.

The period of time allotted to each child event in the second embodiment may also become too short to acquire a sufficient amount of data in the product ion scan analysis if there are many child events. Accordingly, similarly to the first embodiment, if a large number of child events are expected to be spawned from the parent event, the analysis operator additionally sets the minimum length of time to be allotted per child event (minimum child-event execution time) along with the loop time in Step S2.

Provided that the minimum child-event execution time is set by the analysis operator, if the execution time allotted to any of the child events in the previously described manner has become shorter than the minimum child-event execution time, the MS$^n$ analysis execution time allotter 45 modifies the allotment of the execution time to the child events by transposing an appropriate amount of execution time from the child event having the longest execution time among the child events to the child event having a shorter execution time than the minimum child-event execution time so that every child event has an execution time equal to or longer than the minimum child-event execution time.

If there is any child event whose execution time is still shorter than the minimum child-event execution time even after the transposition of the execution time performed by the MS$^n$ analysis execution time allotter 45, the child event having the shortest execution time allotted is cancelled, and the execution times allotted to the child events are recalculated.

Any of the methods for adjusting the execution times of the child events by the MS$^n$ analysis execution time allotter 45 described in the first and second embodiments is a mere example. The system can be configured so as to appropriately perform the readjustment of the execution times according to the purpose of the analysis, presence or absence of an ion of interest, and other factors.

Third Embodiment

Figure 9:
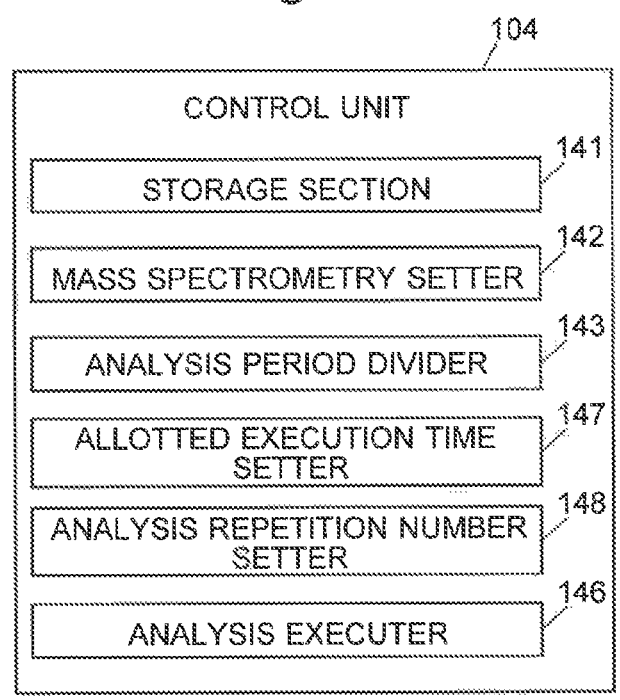
FIG. 9 is the configuration of the control unit in a liquid chromatograph mass spectrometer of the third embodiment.

Hereinafter, a liquid chromatograph mass spectrometer of the third embodiment is described. Since the only difference from the first embodiment in terms of the configuration exists in the control unit, only the configuration of the control unit 104 is shown in FIG. 9, and descriptions concerning the configurations and functions of the liquid chromatograph unit 1 and mass spectrometer unit 2 will be omitted.

The control unit 104 has a storage section 141 and the following functional blocks: a mass spectrometry setter 142, analysis period divider 143, allotted execution time setter 147, analysis repetition number setter 148, and analysis executer 146. The same unit also has the function of controlling the operations of the relevant elements, such as the pump 11 and injector 12 in the liquid chromatograph unit 1 as well as the power supply unit 24 and CID gas supplier (not shown) in the mass spectrometer unit 2, in accordance with the operations of those functional blocks. The control unit 104 is actually a personal computer, which can fulfil the functions as the control unit 104 by executing a data-processing software program previously installed on this computer.

Figure 10:
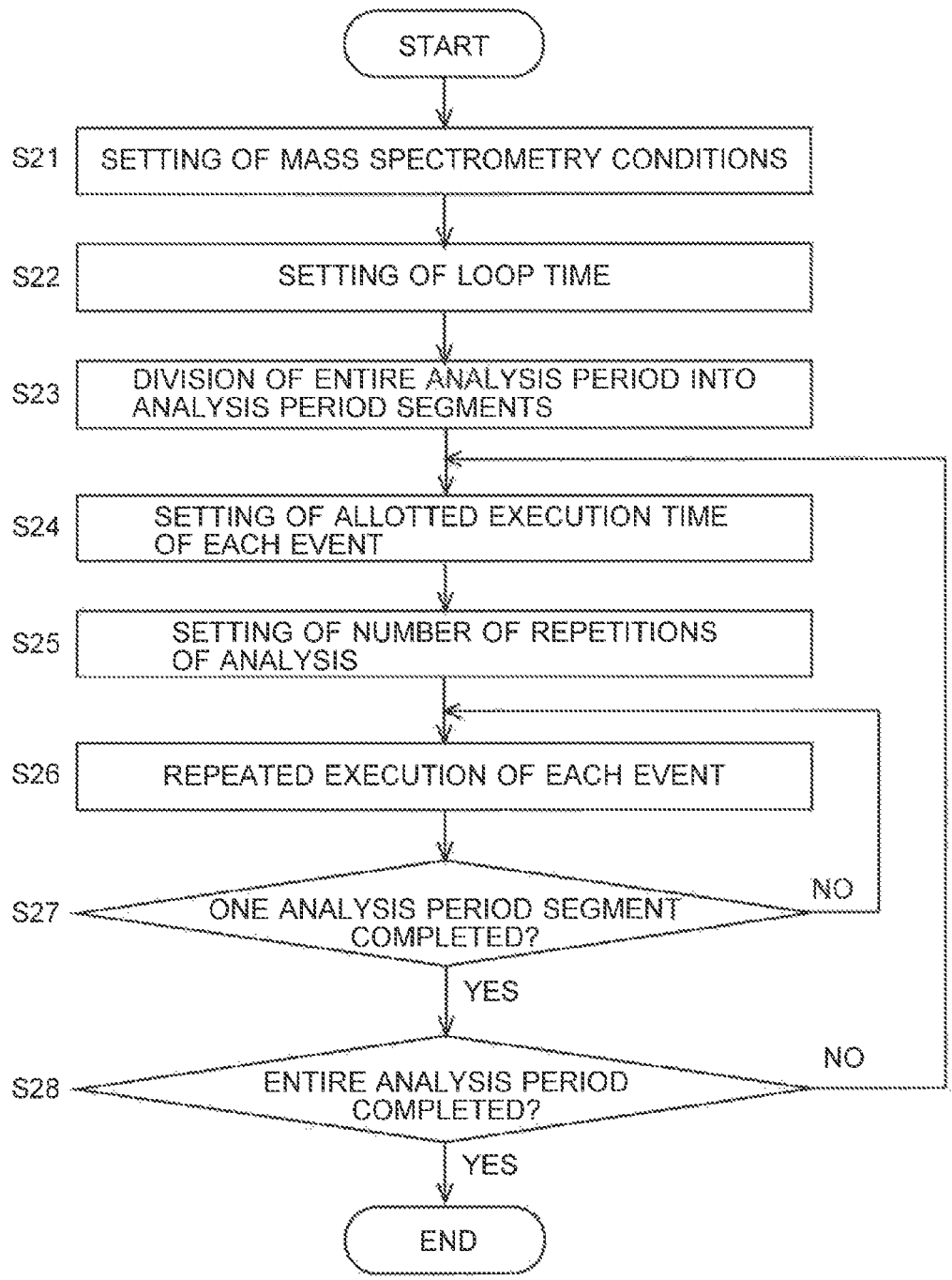
FIG. 10 is a flowchart illustrating the analytical procedure in the liquid chromatograph mass spectrometer of the third embodiment.

A procedure of an analysis using the liquid chromatograph mass spectrometer of the third embodiment is hereinafter described with reference to the flowchart of FIG. 10.

Initially, the mass spectrometry setter 142 displays, on the display unit 7, a window for prompting an analysis operator to set mass spectrometric analysis conditions and loop time. On this display, for one or more target compounds, the analysis operator sets one or more mass spectrometric analyses (events) related to each target compound (Step S21). In the present embodiment, two product ion scan analyses (events 1 and 2) for analyzing compound A, one product ion scan analysis (event 3) for analyzing compound B, and three product ion scan analyses (events 4-6) for analyzing compound C are set. The basic execution time required for performing each event one time in the third embodiment (which is normally equal to the minimum period of time to execute one event) is 100 μsec.

The analysis operator also sets the loop time (in the present embodiment, 100 msec) which determines the data intervals at which the analysis data should be acquired (Step S22). After these setting tasks are completed, the analysis period divider 143 divides the entire analysis period into analysis period segments according to a change in the number of mass spectrometric analyses scheduled in each time window. As a result, an analysis schedule as shown in FIG. 11 is created. The entire analysis period is divided as follows: analysis period segment I (0.0-10.0 min; number of analyses, 2), analysis period segment II (10.0-30.0 min; number of analyses, 3), analysis period segment III (30.0-

40.0 min; number of analyses, 4) and analysis period segment IV (40.0-50.0 min; number of analyses, 3) (Step S23).

Subsequently, the allotted execution time setter 147 divides the loop time by the number of events scheduled in each analysis period segment and sets the allotted execution time for each event (Step S24). For example, for analysis period segment I, 50 msec is allotted to each of the events 1 and 2. FIG. 12 shows the allotted execution time allotted to each event in each analysis period segment.

After the execution times have been allotted to all events, the analysis repetition number setter 148 determines the number of repetitions of each event based on the allotted execution time and the basic execution time of the event (Step S25). In the simplest case, the number obtained by dividing the allotted execution time of each event by the basic execution time of the same event is selected as the number of repetitions of the analysis. Specifically, in the analysis period segment I, the number of repetitions of the analysis is set at 500 for each of the events 1 and 2. In the analysis period segment II, the number of repetitions of the analysis is set at 333 for each of the events 1-3. The same applies in the cases of the analysis period segments III and IV. FIG. 13 shows the number of repetitions of the analysis in each event determined by the present method.

Alternatively, the analysis repetition number setter 148 may determine the number of repetitions of the analysis as follows: For each event, the number of repetitions of the analysis is determined based on the shortest execution time among one or more execution times allotted to that event in one or more analysis period segments in which the event concerned is executed. Specifically, the number of repetitions of the analysis in event 1 is set at 333 based on the allotted execution time in the analysis period segment II. Within the analysis period segment I, the analysis schedule is set so that the analysis is repeated 333 times within 50 msec. For example, this is achieved by slowing the speed of event 1 to expand the execution time to 1.5 times, or inserting an interval of 50 µsec after each scan measurement. It is also possible to set a standby period of 17 msec within the 50-msec execution time allotted to event 1 in the analysis period segment I, and to repeat the analysis 333 times within the remaining 33 msec. The standby period can be appropriately set by the analysis repetition number setter 148 in conjunction with a software application on a computer as well as the present device. FIG. 14 shows the number of repetitions of the analysis in each event determined by the present method. As can be seen in FIG. 14, according to the present method, the same number of repetitions of the analysis is uniformly set for the same event independent of the analysis period segment.

After the numbers of repetitions of the analysis in all events have been determined, the analysis executer 146 repeatedly performs a measurement in which each event is repeated a number of times as indicated by the number of repetitions determined for that event (Step S26). At every completion of one repetition, if the current analysis period segment has been completed ("YES" in Step S27), the analysis executer determines whether or not all analysis period segments have been completed (Step S28). If not all analysis period segments have been completed, the operation proceeds to the next analysis period segment and the sequential process from Step S24 is performed once more.

Any of the previous embodiments is a mere example and can be appropriately changed in line with the spirit of the present invention. Although the first through third embodiments are all concerned with a liquid chromatograph mass spectrometer, a similar configuration can also be adopted in a gas chromatograph mass spectrometer. In place of the tandem mass spectrometer unit, a different type of mass spectrometer may be used, such as an IT-TOF mass spectrometer having an ion trap and time-of-flight mass separation unit. In the first embodiment, since a tandem mass spectrometer unit is used, the parent event is an MS analysis and the child event is an MS/MS analysis. If an IT-TOF mass spectrometer is used, the parent event can be any $MS^{n-1}$ analysis (where n is an integer equal to or greater than two), with the child events being $MS^n$ analyses. In the case of performing an MS scan analysis in the third embodiment, a mass spectrometer with a single mass filter may be used.

The configuration of the first or second embodiment can be combined with that of the third embodiment. For example, provided that the event time of the parent event is fixed by previously setting the number of repetitions of the parent event (and the event time of an MRM measurement or similar quantitative analysis previously determined, if such a measurement is concurrently performed), the number of repetitions of the analysis in each child event can be set by the method of the third embodiment based on the execution time of the child event allotted in Step S7 of the first embodiment and the basic execution time of the same child event.

REFERENCE SIGNS LIST

1 . . . Liquid Chromatograph Unit
   10 . . . Mobile Phase Container
   11 . . . Pump
   12 . . . Injector
   13 . . . Column
2 . . . Mass Spectrometer Unit
   20 . . . Ionization Chamber
   21 . . . First Intermediate Vacuum Chamber
   22 . . . Second Intermediate Vacuum Chamber
   23 . . . Analysis Chamber
      231 . . . Front Quadrupole Mass Filter
      232 . . . Collision Cell
      234 . . . Rear Quadrupole Mass Filter
      235 . . . Ion Detector
   24 . . . Power Supply Unit
4, 104 . . . Control Unit
   41, 141 . . . Storage Section
   42 . . . $MS^{n-1}$ Analysis Setter
   142 . . . Mass Spectrometry Setter
   43, 143 . . . Analysis Period Divider
   44 . . . $MS^n$ Analysis Setter
   45 . . . $MS^n$ Analysis Execution Time Allotter
   46, 146 . . . Analysis Executer
   147 . . . Allotted Execution Time Setter
   148 . . . Analysis Repetition Number Setter
6 . . . Input Unit
7 . . . Display Unit

The invention claimed is:

1. A chromatograph mass spectrometer in which a chromatograph for temporally separating components in a sample is combined with a mass spectrometer capable of performing an $MS^n$ analysis (where n is an integer equal to or greater than two) in which an ion produced by performing, at least one time, a selection and fragmentation of ions produced by ionizing the separated components is subjected to a mass spectrometric analysis, the chromatograph mass spectrometer comprising:

a) an $MS^{n-1}$ analysis setter for allowing an analysis operator to set an analysis execution period in which an $MS^{n-1}$ analysis for a component separated by the chromatograph is performed within an entire analysis period from a beginning to an end of an analysis, and a loop time which is a data acquisition interval common to all $MS^{n-1}$ analyses;
b) an analysis period divider for dividing the entire analysis period into a plurality of analysis period segments according to the number of MSn−1 analyses or contents of analysis conditions of $MS^{n-1}$ analyses to be performed within a same time window;
c) an $MS^n$ analysis setter for performing, in each of the plurality of analysis period segments, an $MS^{n-1}$ analysis to obtain mass spectrum data and extract one or a plurality of mass peaks satisfying a previously set condition, and for scheduling one or a plurality of $MS^n$ analyses in which ions respectively corresponding to the one or plurality of mass peaks are designated as precursor ions;
d) an $MS^n$ analysis execution time allotter for subtracting, in each of the plurality of analysis period segments, an event execution time which is a period of time required for an $MS^{n-1}$ analysis performed within the analysis period segment concerned, from the loop time, and for allotting a remaining time as a period of time in which each of one or a plurality of $MS^n$ analyses scheduled based on the $MS^{n-1}$ analysis is performed one time; and
e) an analysis executer for sequentially and repeatedly performing, in each of the plurality of analysis period segments, an $MS^{n-1}$ analysis and one or a plurality of $MS^n$ analyses scheduled based on the $MS^{n-1}$ analysis.

2. The chromatograph mass spectrometer according to claim 1, wherein:
in a case where a plurality of $MS^{n-1}$ analyses are scheduled in the analysis period segment, the $MS^n$ analysis execution time allotter divides the loop time into loop-time segments which respectively correspond to the plurality of $MS^{n-1}$ analyses, subtracts the event execution time of the corresponding $MS^{n-1}$ analysis from each loop-time segment, and allots the remaining time as an execution time for each of $MS^n$ analyses scheduled based on a result of the $MS^{n-1}$ analysis.

3. The chromatograph mass spectrometer according to claim 1, wherein:
the analysis period divider divides the entire analysis period into a plurality of analysis period segments according to a change in a number of $MS^{n-1}$ analyses scheduled in a same time window and a change in a number of specific-ion analyses for selectively detecting an ion having a specific mass-to-charge ratio; and
the $MS^n$ analysis execution time allotter subtracts, in each of the plurality of analysis period segments, the event execution time plus an execution time for the specific-ion analyses from the loop time, and allots a remaining time as an execution time for each of the one or plurality of $MS^n$ analyses.

4. A chromatograph mass spectrometer in which a chromatograph for temporally separating components in a sample is combined with a mass spectrometer for performing a mass spectrometric analysis of ions produced from the separated components, the chromatograph mass spectrometer comprising:
a) a mass spectrometry setter for allowing an analysis operator to set an analysis execution period in which each of a plurality of mass spectrometric analyses for the components separated by the chromatograph is performed within an entire analysis period from a beginning to an end of an analysis, and a loop time which is a data acquisition interval common to all mass spectrometric analyses;
b) an analysis period divider for dividing the entire analysis period into a plurality of analysis period segments according to a change in a number or analysis condition of mass spectrometric analyses performed within a same time window;
c) an allotted execution time setter for setting, in each of the plurality of analysis period segments, an allotted execution time of each mass spectrometric analysis by dividing the loop time into a number of mass spectrometric analyses scheduled in the analysis period segment concerned;
d) an analysis repetition number setter for setting, in each of the plurality of analysis period segments, a number of repetitions of each mass spectrometric analysis based on the allotted execution time and a basic execution time required for one execution of the mass spectrometric analysis scheduled in the analysis period segment concerned; and
e) an analysis executer for repeatedly executing, in each of the plurality of analysis period segments, an analysis in which each mass spectrometric analysis is performed up to the aforementioned number of repetitions.

5. The chromatograph mass spectrometer according to claim 4, wherein:
the analysis repetition number setter sets, as the number of repetitions of each mass spectrometric analysis, a number obtained by dividing the allotted execution time by the basic execution time.

6. The chromatograph mass spectrometer according to claim 4, wherein:
the analysis repetition number setter sets the number of repetitions of each mass spectrometric analysis so that a mass spectrometric analysis performed over a plurality of analysis period segments under a same condition is always performed with a fixed number of repetitions of the analysis.

7. The chromatograph mass spectrometer according to claim 2, wherein:
the analysis period divider divides the entire analysis period into a plurality of analysis period segments according to a change in a number of $MS^{n-1}$ analyses scheduled in a same time window and a change in a number of specific-ion analyses for selectively detecting an ion having a specific mass-to-charge ratio; and
the $MS^n$ analysis execution time allotter subtracts, in each of the plurality of analysis period segments, the event execution time plus an execution time for the specific-ion analyses from the loop time and allots a remaining time as an execution time for each of the one or plurality of $MS^n$ analyses.

\* \* \* \* \*